US012611534B2

(12) United States Patent
Haddadi et al.

(10) Patent No.:   US 12,611,534 B2
(45) Date of Patent:   *Apr. 28, 2026

(54) OUTPUT PIVOT FOR A MAGNETIC COUPLING CARDIAC PUMP

(71) Applicant: FINEHEART, Pessac (FR)

(72) Inventors: Mohammad Haddadi, Merignac (FR);
Stéphane Garrigue, Begles (FR);
Maryam Haddadi, Merignac (FR);
Arnaud Mascarell, Montbazon (FR)

(73) Assignee: FINEHEART, Pessac (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/458,771

(22) Filed: Aug. 30, 2023

(65) Prior Publication Data

US 2023/0405301 A1      Dec. 21, 2023

Related U.S. Application Data

(63) Continuation of application No. 17/594,244, filed as application No. PCT/EP2020/058870 on Mar. 27, 2020, now Pat. No. 11,779,752.

(30) Foreign Application Priority Data

Apr. 10, 2019    (FR) ...................................... 1903838

(51) Int. Cl.
*A61M 60/174*      (2021.01)
*A61M 60/148*      (2021.01)
      (Continued)
(52) U.S. Cl.
CPC ........ *A61M 60/237* (2021.01); *A61M 60/148* (2021.01); *A61M 60/178* (2021.01);
      (Continued)

(58) Field of Classification Search
CPC .............. A61M 60/205; A61M 60/216; A61M 60/226; A61M 60/232; A61M 60/237;
      (Continued)

(56) References Cited

U.S. PATENT DOCUMENTS

| | | | |
|---|---|---|---|
| 4,957,504 A | 9/1990 | Chardack | |
| 6,135,729 A | 10/2000 | Aber | |

(Continued)

FOREIGN PATENT DOCUMENTS

| | | | |
|---|---|---|---|
| CA | 3068172 | 9/2021 | |
| WO | 2004101029 A1 | 11/2004 | |

(Continued)

OTHER PUBLICATIONS

International Search Report and Written Opinion received for PCT/EP2020/058870, mailed May 28, 2020.

(Continued)

*Primary Examiner* — Jon Eric C Morales
(74) *Attorney, Agent, or Firm* — Greer, Burns & Crain, Ltd

(57)      ABSTRACT

A pump intended to be immersed in a fluid, including a housing, a brushless motor unit formed by a stator in which first magnetic elements are disposed, a rotor having second magnetic elements intended for magnetic coupling with the first magnetic elements of the stator, a transmission shaft connected to the rotor and constituting, in its upper part, a turbine, the turbine includes, at its apex, an output pivot interacting with a guide fastened to the housing, the guide having a complementary shape to that of the output pivot so as to keep the output pivot stable in rotation and to form a space between the output pivot and the guide, and the guide includes a central opening in the axis of rotation of the output pivot for a passage of fluid from the inside of the housing to the outside via the space and the opening.

16 Claims, 3 Drawing Sheets

(51) Int. Cl.

| | |
|---|---|
| *A61M 60/178* | (2021.01) |
| *A61M 60/237* | (2021.01) |
| *A61M 60/422* | (2021.01) |
| *A61M 60/82* | (2021.01) |
| *A61M 60/825* | (2021.01) |

(52) U.S. Cl.
CPC .......... *A61M 60/422* (2021.01); *A61M 60/82* (2021.01); *A61M 60/825* (2021.01)

(58) Field of Classification Search
CPC .............. A61M 60/242; A61M 60/247; A61M 60/253; A61M 60/122; A61M 60/126; A61M 60/165; A61M 60/178; A61M 60/183; A61M 60/82
See application file for complete search history.

(56) References Cited

U.S. PATENT DOCUMENTS

| | | | |
|---|---|---|---|
| 6,234,772 | B1 | 5/2001 | Wampler et al. |
| 2014/0336446 | A1 | 11/2014 | Rodefeld |
| 2018/0311421 | A1 | 11/2018 | Tuseth et al. |

FOREIGN PATENT DOCUMENTS

| | | |
|---|---|---|
| WO | 2013011308 A1 | 1/2013 |
| WO | 2016005803 A2 | 1/2016 |
| WO | 2016146663 A1 | 9/2016 |

OTHER PUBLICATIONS

French Search Report received for Application No. 1903838, dated Jan. 29, 2020.

Notice of Allowance received in Canadian Application No. 3,068,172, dated Apr. 12, 2021.

[Fig. 1]
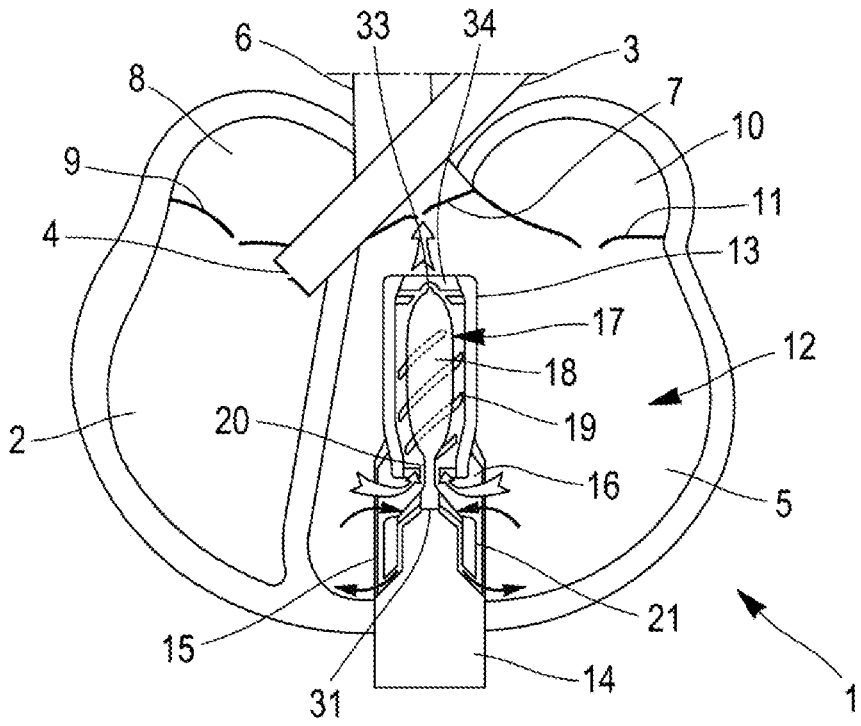
[Fig. 2]
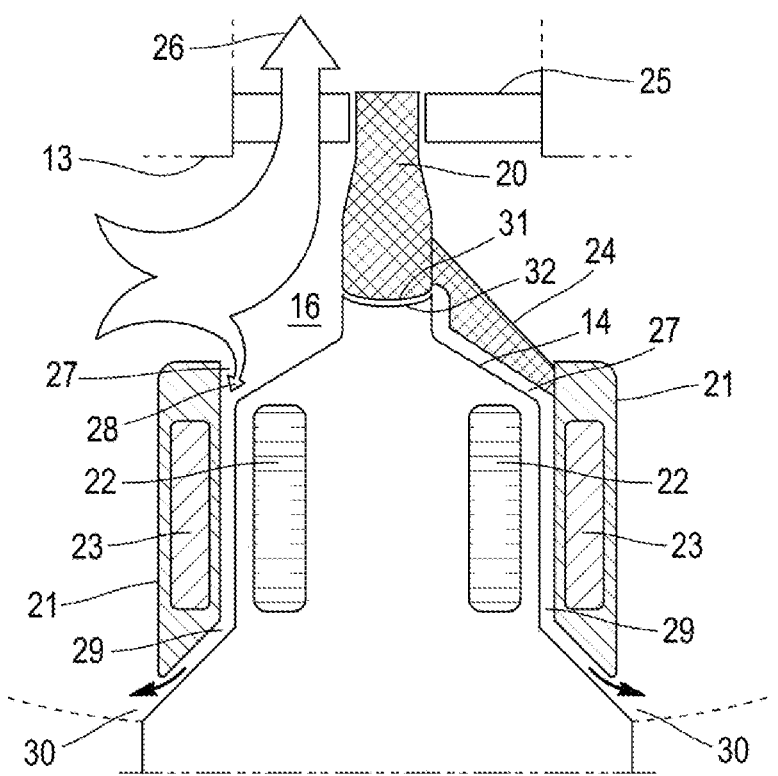

[Fig. 3]
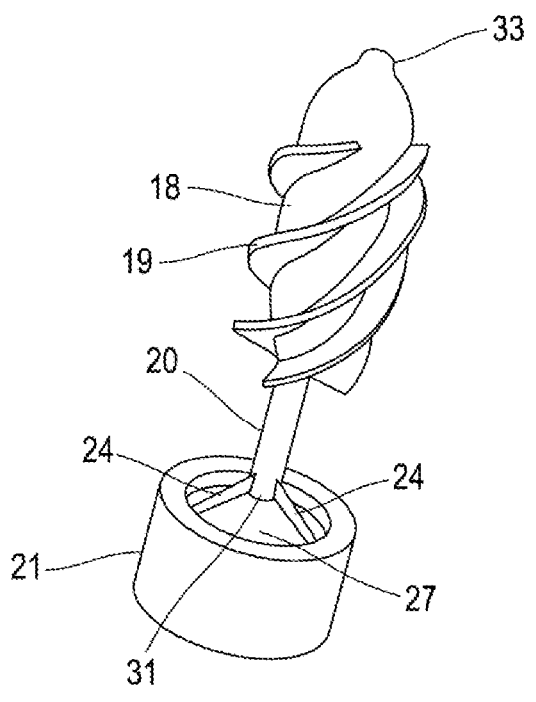
[Fig. 4]
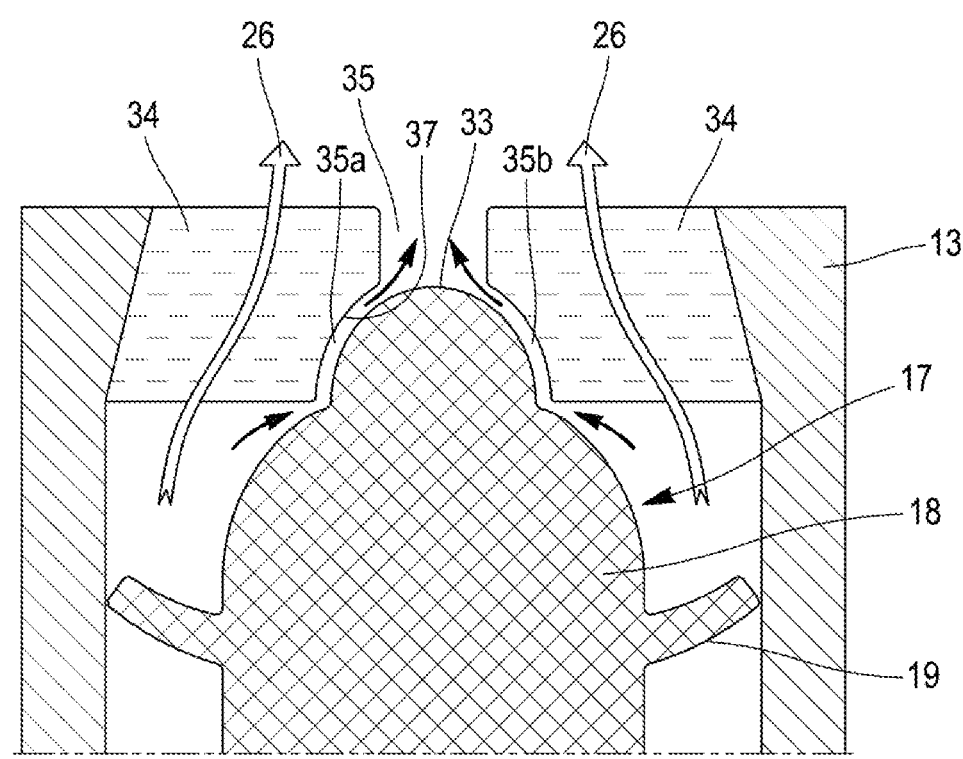

[Fig. 5]
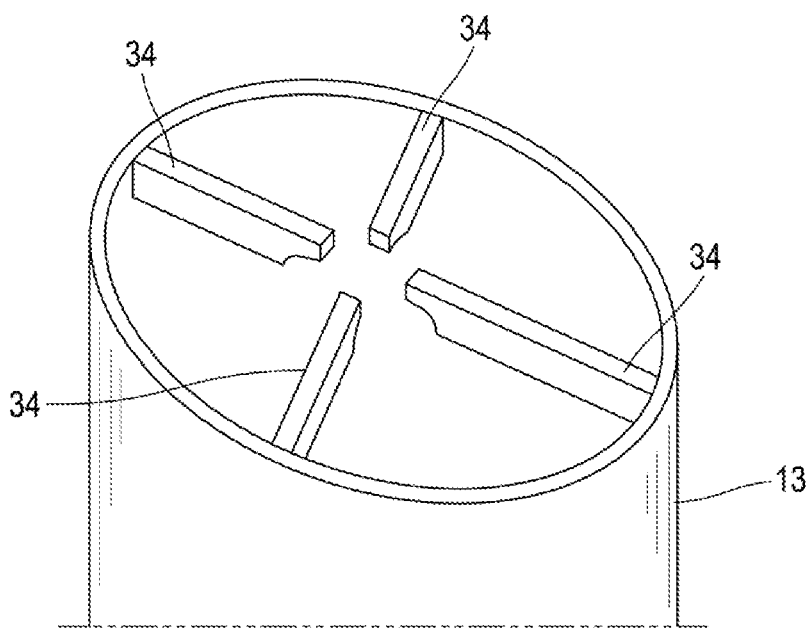
[Fig. 6]
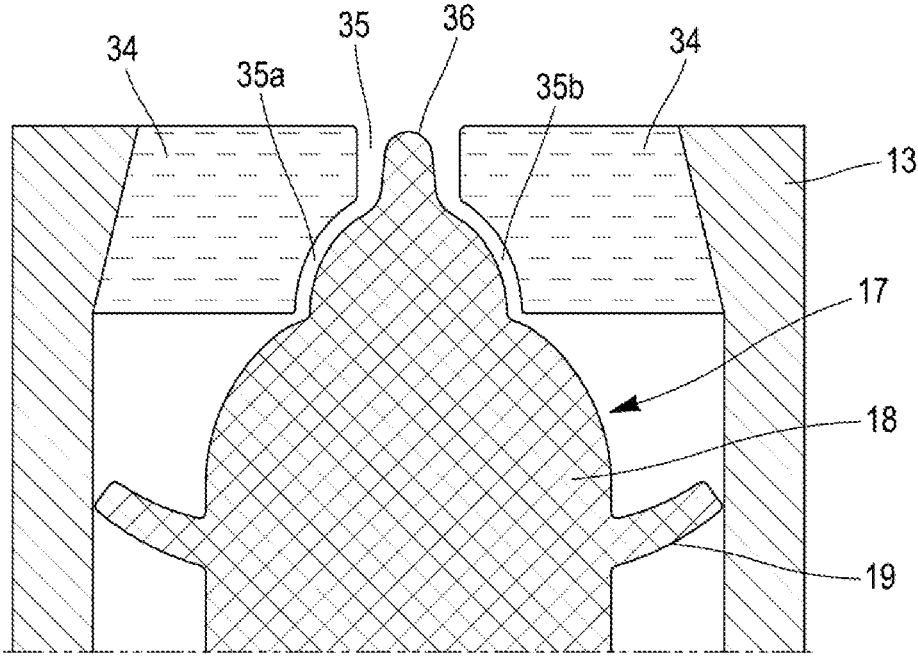

OUTPUT PIVOT FOR A MAGNETIC COUPLING CARDIAC PUMP

RELATED APPLICATIONS

This application is a continuation of, and claims priority under 35 U.S.C. 120 from U.S. application Ser. No. 17/594,244, filed Oct. 7, 2021, which claims the benefit of International Patent Application No. PCT/EP2020/058870 filed on Mar. 27, 2020, and which claims the benefit of French Application No. 1903838, filed Apr. 10, 2019, all of which are incorporated by reference.

BACKGROUND

The present invention relates to a pump, in particular an axial pump, intended to be immersed in a fluid.

The present invention relates more particularly, but not exclusively, to a pump for ventricular assistance. It concerns, for example, a pump supplied by a battery and intended to be inserted into a human body to assist the circulation of the blood.

Heart failure (HF), progressive inability of the heart to supply a blood flow necessary for the metabolic needs of an individual in daily life, is the second cause of mortality in Western countries. The treatment for heart failure, which consists of increasing the blood flow suitably for the needs of the patient, is making progress but still remains inadequate.

Thus, document U.S. Pat. No. 6,234,772 is known, describing an implantable rotary pump. This pump is of the magnetic drive type and makes it possible to increase the blood circulation while preventing any stagnant zones. This document remains silent as to any efficacious implantation of the pump.

Document EP2734251 B1 is also known, describing a miniaturized pump suitable for cardiac implantation. In this document, emphasis is placed on the fact that the blood circulation through the pump must be at a constant flow, without zones of flow stasis that may cause the formation of thromboses. It is recommended to wash the bearings with a constant supply of fresh blood, since the heat and the geometrical constraints of these zones make them potentially predisposed to the formation of thromboses.

These two documents of the prior art relate to a heart pump of the centrifugal type and creating a bypass external to the heart.

SUMMARY

The aim of the present invention is an intraventricular pump that draws blood in the interior of the heart and discharges this blood also in the interior of the heart in the direction of the valves.

An aim of the present invention is also an intraventricular pump the operation of which prevents any creation of thromboses.

At least one of these objectives is achieved with a pump intended to be immersed in a fluid, comprising:
- a casing,
- a brushless motor unit formed by:
  - a. a stator in which first magnetic elements are arranged,
  - b. a rotor comprising second magnetic elements intended for magnetic coupling with the first magnetic elements of the stator, c. a transmission shaft connected to the rotor and constituting an impeller in its top part.

According to the invention, the impeller comprises at its apex an outlet pivot suitable for cooperating with a guide fixed to the casing, this guide having a shape complementary to that of the outlet pivot so as to hold this outlet pivot stable in rotation and to form a clearance between the outlet pivot and the guide. According to the invention, this guide comprises a central opening within the axis of revolution of the outlet pivot for a passage for fluid from the interior of the casing to the exterior, via the clearance and the opening.

The clearance can have a width between 20 and 80 μm. By way of example, it is possible to envisage a clearance of 50 μm and an operating speed of the motor of 4000 rpm.

With the pump according to the invention, the central opening in the guide allows the fluid to pass and prevents the stagnation of fluid in the hollow of the guide when the latter has no opening. With the invention, a void is created between the outlet pivot and the guide for the fluid to pass when the pump is in operation. Advantageously, a flow is thus maintained in this void so that the fluid, which is in particular blood, does not stagnate therein.

This arrangement does not in any way impede the function of the guide, which is to hold the impeller within its axis during the rotations and within the casing.

In operation, there is a clearance between the head of the impeller and the guide. This clearance allows both the rotation of the transmission shaft and at the same time this transmission shaft to be held within its axis of rotation.

Preferably, the outlet pivot comprises a projection entering the central opening of the guide.

The projection makes it possible to guide the fluid efficiently through the central opening.

According to the invention, the guide can be constituted by at least one vane of a straightener and/or of an inducer. In fact, the pump can be equipped with a straightener and/or an inducer arranged in the interior of the casing at the level of the apex of the impeller. It is therefore possible to use a straightener alone, an inducer alone, a straightener and an inducer, or a single component acting as straightener and inducer. The straightener and/or the inducer is fixed to the casing and includes vanes, which for an intraventricular heart pump, direct the outlet fluid towards the aorta.

According to an advantageous characteristic of the invention, the outlet pivot can be convex, having a hemispherical, conical or pyramidal shape.

The pump according to the invention can be an axial pump. I.e. the displacement of the fluid is parallel to the axis of rotation of the rotor, the thrust is axial.

The motor unit can advantageously be a brushless motor with an external rotor.

According to an advantageous characteristic of the invention, in the pump:
- the casing can be provided with a top part forming a propulsion chamber propelling fluid towards the top end, and a bottom part forming a stator and attached in a fixed manner to the top part,
- the pump can comprise at least one side opening between the top part and the bottom part, and can form an inlet chamber for the fluid to enter from the exterior towards the propulsion chamber.
- the rotor can be in the form of a bell at least partially covering the stator head, the bell being capable of having at least one opening in its top part so as to create a reverse flow of the fluid from the inlet chamber right up to the base of the stator via a passage between the rotor and the stator, and the transmission shaft can comprise at least one connecting arm making it possible to hold the bell above the stator, the axis of the transmission shaft being capable of superposition with the axis of rotation of the bell.

With the pump according to the invention, a reverse flow to the main flow intended to pass through the pump is created. The conventional fluid circulation circuit starts by the quantity of operating fluid entering via the inlet chamber, passing into the upper casing, then being propelled towards the top outlet orifice. Furthermore, the present invention is noteworthy in particular for the fact that its arrangement makes it possible to create a flow in the reverse direction to the main flow. This reverse flow is ejected towards the base of the stator and thus acts as a cleaning flow. In other words, by careful arrangement of an opening in the bell, the rotational movement provided for the main flow is used to create a reverse flow.

The bell and the stator advantageously constitute a brushless motor with an external rotor. The mobile part, which in the present invention is the bell, is therefore situated external to the stator and is connected to the transmission shaft, which as will be noted hereinafter, acts as means of propulsion or impeller, to propel the fluid towards the head of the casing and then towards the exterior.

Preferably, the connection between the bell and the transmission shaft is rigid.

According to an advantageous characteristic of the invention, the pump can comprise side vanes arranged between the bell and the transmission shaft and intended to guide the reverse flow in the passage between the rotor and the stator.

These side vanes can be directional or have a curvature. Such an implementation makes it possible to guide the fluid efficiently in the passage between the rotor and the stator and thus create the reverse fluid flow. The dimensions and shapes of the vanes can be determined so as to obtain a continuous or pulsed flow, laminar and without cavitation. With the configuration of the motor, provision is made to reach speeds of 15 to 60 cm/s, as a function of the speed of rotation of the vanes and thus of the motor. Preferably, the passage between the rotor and the stator has a width comprised between 0.4 and 1 mm, for example 0.6 mm.

According to an advantageous characteristic of the invention, the connecting arms constitute said side vanes. These side vanes can be arranged between the internal wall of the bell and the transmission shaft, but they can also be produced in the prolongation of the top end of the bell, similar to a closed bell in which openings have been made, leaving connecting fins. Other embodiments can be envisaged to make the bell and the transmission shaft integral, whether or not using the vanes directly.

Preferably, the opening has a circular shape all round the transmission shaft.

According to an advantageous embodiment, the pump according to the invention can be an intraventricular heart pump intended to be fixed at the apex of a heart, the passage between the rotor and the stator opening directly into the zone where the internal wall of the ventricle and the external wall of the stator meet. Thus, the passage between the rotor and the stator opens into the zone where the risk of thrombosis is high. The reverse fluid flow acts to create fluid circulation in this zone so as to prevent any stagnation.

Furthermore, the pump can have dimensions such that the inlet chamber is located at a distance of 1 to 3 cm from the apex and the outlet orifice of the pump is located in the interior of the ventricle at a distance of 1 to 3 cm upstream of the aortic valve. Such an implementation relates to the field of heart pumps incorporated into the ventricle, pumping and ejecting blood in the heart in the direction of the aortic valve.

According to an advantageous characteristic of the invention, in operation the bell and the transmission shaft are intended to be in magnetic suspension by virtue of the magnetic elements, the bottom end of the transmission shaft and the top end of the stator can then cooperate so as to hold the transmission shaft within its axis of revolution in the rotation phase.

A system of rings and bearings can be used to hold the transmission shaft at the level of the stator, but the present invention preferably uses holding in suspension by pivot.

According to the invention, the top end of the stator can include a concave pivot zone suitable for receiving the convex bottom end, called inlet pivot, of the transmission shaft. With such an implementation, in operation, the fluid passes between the inlet pivot and the pivot zone so as to prevent thrombosis as far as possible while maintaining permanent rinsing of this void between the concave stator and convex rotor parts.

In the idle phase, the transmission shaft can rest on the stator, in this case the inlet pivot and the pivot zone are in contact in particular. But in operation, there is a clearance between the inlet pivot and the pivot zone. This clearance allows both the rotation of the transmission shaft and at the same time this transmission shaft to be held within its axis of rotation.

According to a variant, the top end of the stator can include a convex pivot zone suitable for receiving the concave bottom end, called inlet pivot, of the transmission shaft. The operating principle remains identical in the event that the inlet pivot is convex. Other arrangements can be envisaged, with more or less complex shapes, but allowing both free rotation and holding within the axis of revolution (or rotation) of the transmission shaft.

According to an advantageous embodiment of the invention, the transmission shaft can include, or be connected to, a top part equipped with vanes, for example helical vanes, allowing main fluid to be drawn from the inlet chamber to the outlet of the pump.

In particular, in addition to the foregoing, the pump according to the invention can comprise:

at the inlet of the top part of the casing, an inductor equipped with guide vanes in order to make the flow of the fluid linear in the direction of the top part of the transmission shaft; the impeller comprising a central body with a flared shape, intended to create kinetic energy;

at least one helical vane, produced around said central body; this helical vane having a flared external profile and including turns having an increasing winding pitch that tends towards infinity, the internal volume of the casing being complementary to the flared shape of said at least one helical vane.

The transmission shaft then drives an impeller or a propeller equipped with vanes in order to draw the fluid efficiently from the inlet chamber and eject it at the outlet of the pump. Accordingly, the pump acts to circulate fluid in the main direction. At the same time, the reverse fluid flow makes it possible to stir the fluid present in the base of the stator and thus prevent stagnation, the source of potential thromboses.

Advantageously, the pump according to the invention can be an intraventricular heart pump intended to be fixed at the apex of a left ventricle or of a right ventricle or of a systemic ventricle.

BRIEF DESCRIPTION OF THE DRAWINGS

Other advantages and characteristics of the invention will become apparent on examination of the detailed description of an embodiment that is in no way limitative, and from the attached drawings, in which:

FIG. 1 is a general view of an intraventricular heart pump according to the invention, FIG. 2 is a diagrammatic view of a bottom part of the pump according to the invention, FIG. 3 is a diagrammatic view of an impeller according to the invention, FIG. 4 is a diagrammatic view of a top part of the pump comprising a rotation pivot of the impeller according to the invention, FIG. 5 is a very simplified diagrammatic view of a straightener according to the invention, FIG. 6 is a diagrammatic view of a top part of the pump illustrating another embodiment of a rotation pivot of the impeller according to the invention.

DETAILED DESCRIPTION

The embodiments that will be described hereinafter are in no way limitative; variants of the invention can in particular be implemented comprising only a selection of the characteristics described hereinafter, in isolation from the other characteristics described, if this selection of characteristics is sufficient to confer a technical advantage or to differentiate the invention with respect to the state of the prior art. This selection comprises at least one, preferably functional, characteristic without structural details, or with only a part of the structural details if this part alone is sufficient to confer a technical advantage or to differentiate the invention with respect to the state of the prior art.

In particular, all the variants and all the embodiments described are intended to be combined together in any combination, if there is no objection thereto from a technical point of view.

In the figures, elements common to several figures retain the same reference.

FIG. 1 shows an intraventricular heart pump.

The heart as a whole is denoted by the reference 1. The right ventricle 2, which has the function of ejecting the blood towards the pulmonary artery 3 via the sigmoid valves 4, is shown. The left ventricle 5 has the function of carrying out the systemic circulation by ejecting the oxygenated blood towards the aorta 6 via sigmoid valves 7.

The right atrium 8 feeds the right ventricle 2 with blood via atriopulmonary valves 9. The left atrium 10 feeds the left ventricle 5 with blood via the atriopulmonary valves 11.

The pump as a whole according to the invention is referenced 12. It is fixed at the apex of the left ventricle 5. It can be connected wired or wirelessly to a management unit (not shown) external to the heart. It can be connected to one or more probes or sensors (not shown) for detecting the heart rate or other.

The bottom part of the pump casing the motor can be partially external to the heart, partially within the thickness of the apex or entirely within the heart. In the example in FIG. 1, the bottom part of the pump is partially external to the heart, which can be an advantage for maintenance of the motor in particular.

The pump comprises a casing constituted by a top part 13 rigidly attached to a bottom part 14 by means of connecting elements 15. These connecting elements can comprise one or more rods 15 connecting the two parts 13 and 14 while leaving wide passages for the blood.

The bottom part 14 constitutes the stator of a motor. The casing is intended to remain fixed. Between the top part 13 and the bottom part 14, there is an inlet chamber 16 which is an open space, only obstructed by the connecting elements 15. In operation, the pump is intended to draw the blood contained in the ventricle 5 via the inlet chamber 16, convey it through the top part 13 of the casing and eject it by the top outlet towards the valve 7.

In order to draw the blood, the pump comprises an impeller 17 designed on the basis of an oblong body 18 around which is wound one or more helical vanes 19. In rotation, the impeller draws the blood and propels it towards the outlet. This is the main function of the pump. The main flow is therefore that which is pumped by the impeller 17.

The impeller is borne by a transmission shaft 20 which includes at the end opposite the impeller, a bell 21. The assembly of impeller 17, transmission shaft 20 and bell 21 is rigid and suitable for performing rotations. To this end, the bell 21 constitutes the rotor of the motor formed with the fixed stator 14. This motor 14 and 21 is a motor of the brushless type with an external rotor. This is a synchronous machine equipped with an electronic control system (not shown), accessible externally to the heart or not.

The impeller is suitable for performing rotational movements about its axis and relative to the casing 13, 14, which remains fixed. An inlet pivot 31 and an outlet pivot 33 are located within the axis of rotation of the impeller and hold the impeller within its axis when it is in magnetic suspension during the rotational movements. In a variant (not shown) one or both of the two pivot zones can comprise connections with bearings allowing the rotation of the impeller.

FIG. 2 shows the inlet chamber 16 and the motor 14, 21 in a little more detail. The inlet chamber 16 is the open space between the transmission shaft 20, the bell 21 and the top casing 13.

Stator windings 22 are arranged in the stator 14 close to permanent magnets 23 arranged in the bell 21, the assembly being designed in combination with other components, in particular electronic components (not shown) for constituting a brushless motor.

The transmission shaft 20 is rigidly connected to the bell 21 by means of side vanes 24. Activation of the stator magnetic field by electronic means results in rotation of the bell 21 and consequently rotation of the transmission shaft 20 as well as that of the impeller 17. The fluid contained in the ventricle and all around the pump enters by the inlet chamber 16 and continues in the top part 13 of the casing via an inductor 25. This upward fluid flow as shown in FIG. 2 is the main flow 26. According to the invention, the bell 21 has a top opening 27 through which a portion of the fluid is made to circulate. This is a descending reverse flow 28 according to the diagram in FIG. 2. This reverse flow is maintained as a continuous laminar flow by virtue of the side vanes 24 which guide it towards a passage 29 present between the bell 21 and the stator 14. This passage 29 brings the reverse flow 28 right into the zone 30 at the foot of the stator. This zone 30 constitutes a corner in which the fluid, i.e. the blood in the present example, can stagnate. Generating a reverse flow of this type by using the rotational movement of the impeller makes it possible to maintain movement in this corner, therefore preventing stagnation of the blood. Thus any thrombosis formation is prevented.

The side vane 24 has a connecting function between the transmission shaft 20 and the bell 21 and a function of guiding the blood towards the passage 29. This side vane 24 is connected by one end to a top part of the bell 21, extends above this bell, and is connected by another end to a low part of the transmission shaft 20. Arranged in this way, the side vane 24 has a central part in the inlet chamber 16. The passage 29 is the gap between the rotor and the stator and opens out at the level of the apex. The passage 29 does not include a pronounced curve so as to avoid creating a stagnant zone.

In rotation, the transmission shaft is in magnetic suspension. The bottom end of the transmission shaft includes a convex rounded zone and constitutes the inlet pivot 31. The top part of the stator has a concave rounded shape and constitutes a pivot zone 32. The inlet pivot 31 and the pivot zone 32 have complementary shapes which can marry together perfectly. In the idle position, the inlet pivot 31 rests in the pivot zone 32. In rotation, the transmission shaft is in suspension and a clearance is created between the inlet pivot 31 and the pivot zone 32. However, the pivot zone 32 is shaped so as to hold the inlet pivot 31 within its axis of rotation. The convex shape of the inlet pivot 31 moreover allows the reverse flow to pass in the clearance between the inlet pivot 31 and the pivot zone 32. This allows permanent cleaning of this zone and therefore a low risk of blood stagnating.

FIG. 3 shows the impeller 17 in a little more detail, connected to the transmission shaft 20 and to the bell 21. The outlet pivot 33, in the shape of a hemisphere, is located at the apex of the impeller and within the axis of rotation.

The helical vanes 19 surround the body 18 from the foot until covering approximately three-quarters of the body 18. The apex of the impeller is devoid of vanes.

The transmission shaft 20 is solidly connected to side vanes 24, two of which are visible and a third hidden. There are three side vanes, but it is possible to have only one, two or more than three. In any event, the side vanes 24 must leave openings 27 so that the fluid can enter the interior of the bell 21. In the example shown in the figures, the inlet pivot 31 is located above the bell 21, but other embodiments can be envisaged where the inlet pivot is arranged in the interior of the bell 21.

With the pump according to the invention, the transmission shaft is not mechanically connected to the stator of the motor.

FIG. 4 shows a top part of the pump in a little more detail. The impeller 17 can be seen, which propels the main flow 26 towards the outlet of the pump by means of the vanes 19. Holding the impeller in place is ensured by the presence of the outlet pivot 33 having a convex rounded shape. This is a hemisphere. This outlet pivot 33 is intended to perform rotational movements, together with the impeller, while remaining confined within a niche produced in a fixed guide 34 connected to the top part of the casing 13. The niche is formed by cut-outs 37 produced in the guide 34. The shape of the niche is complementary to that of the outlet pivot 33. Shapes other than hemispherical can be envisaged, such as for example a conical shape. This niche constitutes a pivot zone for the outlet pivot 33.

The two pivot zones 32 and 37 make it possible to hold the impeller and transmission shaft assembly within its axis of rotation and within a vertical range of movement (as per the direction in the diagrams) that is quite limited. Similarly, in order to avoid stagnation of the blood in the guide 34, an opening 35 is made at the centre of this guide so as to allow the blood to circulate and not to stagnate in the guide. In fact, between the zone 37, forming a guide, and the outlet pivot 33, a clearance 35a, 35b is located, or a void for the fluid to pass when the pump is in operation. By action of the motor, a flow is maintained in this void so that the blood cannot stagnate therein. A passage 35a, 35b is created from the interior of the casing right into the opening 35 via the void.

FIG. 5 is a very simplified diagrammatic view of the outlet of the pump. Guides 34, which are vanes fixed to the internal wall of the casing 13, are shown. These are four vanes 34 arranged in a cross and spaced apart from one another in the central zone so that this central zone constitutes the niche and the opening 35. The set of vanes 34 constitutes a straightener arranged at the outlet of the pump so as to increase the speed and to give the fluid a predetermined profile at the outlet. This straightener can be preceded by an outlet inducer (not shown in FIG. 4), the function of which is to increase the pressure of the fluid so as to evacuate the fluid from the rotor towards the exterior by converting the kinetic energy created by the rotor into potential energy.

With such an implementation, the fluid passes mainly as a flow 26 as shown in FIG. 4, but it also passes via the opening 35.

For improved stability of the impeller, in the embodiment illustrated in FIG. 6 an outlet pivot 33 is shown, equipped within its prolongation with a projection 36.

This projection 36 enters the opening 35 partially or completely until it extends beyond the end of the guide. The blood flow is propelled along the external wall of the outlet pivot and its projection, through the opening 35 via the clearances 35a and 35b.

With the pump according to the invention, the outlet pivot is contained in a niche with a central opening. This arrangement makes it possible to eliminate any blood stagnation zone that could give rise to possible thromboses.

The preferred method of operation of the pump is pulsed-mode motor operation. With such operation, speeds of 1500 to 7000 rpm are envisaged.

Of course, the invention is not limited to the examples which have just been described and numerous adjustments can be made to these examples without exceeding the scope of the invention. For example, one and/or the other of the pivots can be constituted in a single piece with the impeller or the transmission shaft, but one and/or the other can also be composed of a material different from that of the impeller and of the transmission shaft; this part would be fixed permanently and would be in rotation with the impeller and the transmission shaft. This material can be ceramic or a thermostable plastic material such as polyetheretherketone (PEEK).

The pivot zone on the stator and/or the part 37 of the guide can be constituted by a material made from titanium.

What is claimed is:

1. A pump intended to be immersed in a fluid, the pump comprising an upper part and a lower part when said pump is positioned vertically, the pump also comprising:

a casing;

a brushless motor unit at a lower part of the pump formed by:

a stator in which first magnetic elements are arranged, a rotor comprising second magnetic elements intended for magnetic coupling with the first magnetic elements of the stator;

a transmission shaft connected to the rotor and constituting an impeller in its top part, the impeller being at the upper part of the pump;

at the upper part of the pump, the impeller comprises at an apex, an outlet pivot suitable for cooperating with a guide fixed to the casing, said guide including a cavity having a shape complementary to that of the outlet pivot so as to hold said pivot stable in rotation and to form a clearance between the outlet pivot and the guide, and in that said guide comprises a central opening via the cavity within the axis of revolution of the outlet pivot for a passage for the fluid from the interior of the casing to the exterior, via the clearance and the opening, and in that the outlet pivot is convex, having a hemispherical, conical or pyramidal shape, and wherein the guide constitutes the outlet of the pump.

2. The pump according to claim 1, characterized in that the guide is constituted by at least one vane of a straightener and/or an inducer.

3. The pump according to claim 1, characterized in that it is an axial pump.

4. The pump according to claim 1, characterized in that the motor unit is a brushless motor with an external rotor.

5. The pump according to claim 1, characterized in that:

the casing is provided with a top part comprising an upper end, the upper part of the casing forming a propulsion chamber propelling fluid towards the top end of the casing, and a bottom part, the bottom part forming a stator and being attached in a fixed manner to the top part of the casing;

the pump comprises at least one side opening between the top part of the casing and the bottom part of the casing, and forming an inlet chamber for the fluid to enter from the exterior towards the propulsion chamber;

the rotor is in the form of a bell at least partially covering the stator head, h bell having at least one opening in its top part so as to create a reverse flow of the fluid from the inlet chamber right up to the base of the stator via a passage between the rotor and the stator; and the transmission shaft comprises at least one connecting arm making it possible to hold the bell above the stator, the axis of the transmission shaft being superposed with the axis of rotation of the bell.

6. The pump according to claim 5, characterized in that it comprises side vanes arranged between the bell and the transmission shaft and intended to guide the reverse flow in the passage between the rotor and the stator.

7. The pump according to claim 6, characterized in that said side vanes are directional or have a curvature.

8. The pump according to claim 6, characterized in that the at least one connecting arm constitutes said side vanes.

9. The pump according to claim 5, characterized in that it is an intraventricular heart pump intended to be fixed at the apex of a heart, the passage between the rotor and the stator opening directly in the zone where the internal wall of the ventricle and the external wall of the stator meet.

10. The pump according to claim 9, characterized in that said pump has dimensions such that the inlet chamber is located at a distance of 1 to 3 cm from the apex and the outlet orifice of the pump is located in the interior of the ventricle at a distance of 1 to 3 cm upstream of the aortic valve.

11. The pump according to claim 5, characterized in that in operation the bell and the transmission shaft are intended to be in magnetic suspension by virtue of the magnetic elements, the bottom end of the transmission shaft and the top end of the stator cooperating so as to hold the transmission shaft within its axis of revolution in the rotation phase.

12. The pump according to claim 11, characterized in that the top end of the stator includes a concave pivot zone suitable for receiving the convex bottom end, called inlet pivot, of the transmission shaft.

13. The pump according to claim 11, characterized in that the top end of the stator includes a convex pivot zone suitable for receiving the concave bottom end, called inlet pivot, of the transmission shaft.

14. The pump according to claim 5, characterized in that the transmission shaft includes a top part equipped with vanes, allowing main fluid to be drawn from the inlet chamber to the outlet of the pump.

15. The pump according to claim 14, characterized in that said pump comprises:

at an inlet of the top part of the casing, an inductor equipped with guide vanes in order to make the flow of the fluid linear in the direction of the top part of the transmission shaft;

the impeller comprising a central body with a flared shape, intended to create kinetic energy;

at least one helical vane, produced around said central body; this helical vane having a flared external profile and including turns having an increasing winding pitch that tends towards infinity; the internal volume of the casing being complementary to the flared shape of said at least one helical vane.

16. The pump according to claim 1, characterized in that the intraventricular heart pump is intended to be fixed at the apex of a left ventricle or of a right ventricle or of a systemic ventricle.

\* \* \* \* \*